United States Patent [19]

Akimoto et al.

[11] Patent Number: 5,314,812

[45] Date of Patent: * May 24, 1994

[54] MICROBIOLOGICAL PROCESS FOR PRODUCTION OF FATTY ACIDS HAVING HIGH DEGREE OF UNSATURATION WITH ECHINOSPORANGIUM

[75] Inventors: Kengo Akimoto, Mishima; Yoshifumi Shinmen, Otokuni; Hideaki Yamada; Sakayu Shimizu, both of Kyoto, all of Japan

[73] Assignee: Suntory Limited, Osaka, Japan

[ * ] Notice: The portion of the term of this patent subsequent to Apr. 10, 2007 has been disclaimed.

[21] Appl. No.: 649,144

[22] Filed: Feb. 1, 1991

Related U.S. Application Data

[63] Continuation of Ser. No. 378,295, Jul. 11, 1989, abandoned.

[30] Foreign Application Priority Data

Jul. 13, 1988 [JP] Japan ................................ 63-172589

[51] Int. Cl.$^5$ .......................... C12P 7/64; C12N 1/14; C12N 9/60
[52] U.S. Cl. .................... 435/134; 435/135; 435/136; 435/254.1; 435/171; 435/244
[58] Field of Search ............ 435/134, 135, 136, 254.1, 435/171, 911, 244, 146

[56] References Cited

U.S. PATENT DOCUMENTS 4,783,408  11/1988  Suzuki et al. ........................ 435/911
4,916,066   4/1990  Akimoto ............................. 435/911

OTHER PUBLICATIONS

Ellis et al., "Two New Families of Mucorales", *Mycologia*, vol. 66(1) pp. 87–95, 1974.
Malloch, "A New Genus of Mucorales", *Mycologia*, vol. 59(2) pp. 326–329, 1967.
Shimizu et al., "Stimulatory effect of peanut oil . . . ", *Agric. Biol. Chem.*, vol. 53(5) pp. 1437–1438, 1989.
Ratledge, "Fermentation Substrates" in *Annual Reports on Fermentation Processes*, ed. Perlman, vol. 1, 1977, pp. 65–67.

*Primary Examiner*—Irene Marx
*Attorney, Agent, or Firm*—Burns, Doane, Swecker & Mathis

[57] ABSTRACT

A process for the production of a highly unsaturated fatty acid comprising the steps of culturing a microorganism belonging to the genus Echinosporangium and capable of synthesizing highly unsaturated fatty acids to produce highly unsaturated fatty acids or a lipid containing highly unsaturated fatty acid, and recovering the highly unsaturated fatty acid; and a process for the production of a lipid containing highly unsaturated fatty acids comprising the steps of culturing a microorganism belonging to the genus Echinosporangium and capable of synthesizing highly unsaturated fatty acids to produce a lipid containing highly unsaturated fatty acids, and recovering the lipid containing highly unsaturated fatty acids.

10 Claims, No Drawings

MICROBIOLOGICAL PROCESS FOR PRODUCTION OF FATTY ACIDS HAVING HIGH DEGREE OF UNSATURATION WITH ECHINOSPORANGIUM

This application is a continuation of application Ser. No. 07/378,295, filed Jul. 11, 1989, now abandoned.

BACKGROUND OF THE INVENTION

1. Field of the Invention

The present invention relates to a process for the production of a fatty acid having a high degree of unsaturation and a lipid containing such unsaturated fatty acids.

2. Description of the Related Art

Processes for the production of fatty acids having a high degree of unsaturation using various microorganisms are known, but a process for the production of fatty acids having a high degree of unsaturation (hereinafter, highly unsaturated fatty acids) by a microorganism belonging to the genus Echinosporangium is not known.

SUMMARY OF THE INVENTION

Accordingly, the present invention provides new processes for the production of highly unsaturated fatty acids and a lipid comprising highly unsaturated fatty acids by a microorganism belonging to the genus Echinosporangium.

More specifically the present invention provides a process for the production of a highly unsaturated fatty acid comprising the steps of:

culturing a microorganism belonging to the genus Echinosporangium and capable of synthesizing highly unsaturated fatty acids to produce highly unsaturated fatty acids or a lipid containing highly unsaturated fatty acids; and recovering the highly unsaturated fatty acids.

The present invention also provides a process for the production of a lipid containing highly unsaturated fatty acids comprising the steps of:

culturing a microorganism belonging to the genus Echinosporangium and capable of synthesizing highly unsaturated fatty acids to produce a lipid containing highly unsaturated fatty acids; and recovering the lipid containing highly unsaturated fatty acids.

DESCRIPTION OF THE PREFERRED EMBODIMENT

In the present invention, the term "highly unsaturated fatty acid" denotes a fatty acid containing at least three double bonds in a carbon chain and having preferably 18 to 22 carbon atoms. Such highly unsaturated fatty acids include, for example, $\alpha$-linolenic acid, $\gamma$-linolenic acid, bishomo-$\gamma$-linolenic acid, arachidonic acid, eicosapentaenoic acid, docosahexaenoic acid.

In the present invention, as a producer microorganism, any strain belonging to the genus Echinosporangium capable of producing highly unsaturated fatty acids can be used. For example, *Echinosporangium transversalis* ATCC 16960; NRRL 3116, and *Echinosporangium transversalis* ATCC 18036; NRRL 5525. These strains can be obtained without limitation from the American Type Culture Collection (ATCC). *Echinosporangium transversalis* strain ATCC 16960 deposited with the ATCC is the same strain as NRRL 3116 deposited with the NRRL. Similarly, *Echinosporangium transversalis* strain ATCC 18036 deposited with the ATCC is the same as strain NRRL 5525 deposited with the NRRL. These strains are available from both the ATCC and NRRL whose addresses are:

American Type Culture Collection [ATCC]
12301 Parklawn Drive
Rockville, Md. 20852, USA Agricultural Research Service Culture Collection (NRRL
Northern Regional Research Center 1815 No. University Street
Peoria, Ill. 61604, USA For the production of highly unsaturated fatty acids and a lipid containing highly unsaturated fatty acids, spores, mycelia, or a preculture are used as an inoculum for culturing the present strains. The medium used may be a liquid or solid medium. A liquid medium contains as a carbon source, for example, glucose, fructose, xylose, saccharose, maltose, soluble starch, molasses, glycerol, or mannitol. Nitrogen sources include organic substances such as peptone, yeast extract, meat extract, casamino acid, corn steep liquor, and inorganic substances such as sodium nitrate, ammonium nitrate, ammonium sulfate, and the like. If necessary, inorganic salts such as phosphate salts, magnesium sulfate, ferrous sulfate and cupric sulfate, and vitamins may be included in a medium. The concentration of these components is selected so that such components do not adversely affect the growth of the microorganism used. Practically, the concentration of the carbon source is 0.1 to 30% by weight, preferably 1 to 10% by weight, relative to the total weight of the medium. The concentration of the nitrogen source is 0.01 to 5% by weight, preferably 0.1 to 2% by weight, relative to the total weight of the medium.

To enhance the production of target fatty acids, in addition to the above-mentioned medium components, hydrocarbons, such as hexadecane or octadecane; fatty acids such as oleic acid or linoleic acid, or salts thereof, such as sodium salt or potassium salt; or oil such as olive oil, cottonseed oil or coconut oil, either alone of in combination can be added. These additives are preferably added to a medium in an amount of 0.01% to 20%, and may be added to a medium at the start of culturing or during the culturing. More particularly, hydrocarbons are preferably added to a medium at the start of culturing, and fatty acids or salts thereof, or fats, are preferably added at the start of and/or during culturing. When such an additive is used during culturing, it is added at one time, stepwise, or continuously.

Moreover, to increase the yield of bishomo-$\gamma$-linolenic acid, a microorganism belonging to the genus Echinosporangium and capable of producing arachidonic acid is preferably cultured in the presence of an additive such as sesame oil, peanut oil or mixture thereof, or an effective ingredient derived from peanut oil or sesame oil. These oils can be in a crude form or a purified form.

The effective ingredient derived from sesame oil can be an extract from sesame oil. To obtain the extract, sesame oil is extracted with an organic solvent which is substantially immiscible with the sesame oil and can extract and dissolve effective ingredients. The organic solvents are, for example, acetone, methyl ethyl ketone, diethyl ketone, methanol, ethanol, and the like. To extract the effective ingredients, for example, sesame oil and the solvent are homogeneously mixed, and the mixture is allowed to stand at a low temperature. Phases are separated by a conventional procedure such as centrifugation to obtain an organic phase, which is then evaporated to obtain an extract. Alternatively, an extract useful for the present invention can be obtained from sesame seeds. In this case, sesame seeds, if necessary after grinding, are extracted with any solvent able to extract the sesame oil, for example, an organic solvent described above. After separating the solvent from the residue, the solvent is evaporated to obtain an extract. Extracts obtained from sesame oil or sesame seeds include lignans such as sesamin, sesaminol, episesamin, episesaminol, sesamolin, 2-(3,4-methyl-enedioxypheny)-6-(3-methoxy-4-hydroxyphenyl) -3,7-dioxabicyclo [3.3.0] octane, 2,6-bis-(3-methoxy-4-hydroxyphenyl)-3,7-dioxabicyclo [3.3.0] octane, 2-(3,4-methylenedioxyphenyl)-6-(3-methoxy-4-hydroxy-phenoxy)-3,7-dioxabicyclo [3.3.0] octane. Therefore, in accordance with the present invention, the above-mentioned compound alone, or any combination of at least two of the above-mentioned compounds, can be used as the additive. All of the above-mentioned compounds are known and are commercially available. Alternatively, these compounds can be isolated from the above-mentioned extract from sesame oil or sesame seeds. To this end, the extract can be separated by a conventional procedure, such as column chromatography, high performance liquid chromatography, distillation, crystallization, or a combination thereof.

Moreover, the additives used in the present invention include extracts from various kinds of plants, for example, spicy plants such as Tarragon, Dill Seed, Parsley, Turmeric, Nutmeg, and the like. Moreover, extracts can be prepared from spices made from these plants. These extracts can be prepared by extracting the above-mentioned materials with a conventional solvent such as dichloromethane, ethanol, methanol, ethyl ether or the like.

The amount of additive to be added to a culture medium is approximately as follows. Sesame oil, peanut oil, or a total amount of a mixture thereof is used at 0.001 to 10% by weight, preferably 0.5 to 10% by weight relative to the amount of the medium. The extract from sesame oil or sesame seeds is used in an amount of $3 \times 10^{-3}$ to $3 \times 10^{-1}$% by weight relative to the amount of the medium. The above-mentioned lignan compounds are used in an amount of $1 \times 10^{-3}$ to $1 \times 10^{-1}$% by weight relative to the amount of the medium. Where a mixture of two or more lignans is used, this amount is intended to be a total amount of the mixture.

The above-mentioned additive can be added to a culture medium before inoculation, or immediately after inoculation and before the onset of culturing. Alternatively, the additive can be added to a medium during culturing, or both before the onset of culturing and during culturing. When such an additive is used during culturing, it is added at one time, stepwise, or continuously.

The culturing temperature ranges from 5° C. to 40° C., preferably 20° C. to 30° C., and a pH value of the medium is 4 to 10, preferably 6 to 9.

Culturing is preferably carried out with aeration and/or agitation, with shaking in a liquid medium, or with standing, and is usually carried out for 2 to 10 days.

When culturing is carried out on a solid medium, the solid medium is composed of wheat bran, chaff or rice bran supplemented with water in an amount of 50 to 100% by weight relative to the wheat bran, chaff or rice bran. If necessary, the medium is supplemented with a small amount of nitrogen source, inorganic salts, and/or minor nutrients. Culturing is carried out at a temperature of 5° C. to 40° C., preferably 20° C. to 30 ° C., for 3 to 14 days.

During culturing, a lipid containing highly unsaturated fatty acids is intracellularly accumulated. Where culturing is carried out in a liquid medium, highly unsaturated fatty acid is recovered, for example, as follows. After culturing cells are collected from the culture broth by a conventional means such as filtration or centrifugation, the cells are washed with water, and preferably, the washed cells are dried.

Drying is carried out by, for example, lyopilization or air-drying. The dried product is treated with an organic solvent or a mixture thereof, preferably under a nitrogen stream to extract a lipid containing highly unsaturated fatty acid. The organic solvent or mixture thereof is, for example, ethers such as ethyl ether, hydrocarbons such as hexane, alcohols such as methanol or ethanol, halo-hydrocarbons such as chloroform or dichloromethane, petroleum ether, as well as a mixture of chloroform, methanol and water, or a combination of methanol and petroleum ether alternately used. By distilling off the solvent, a lipid containing highly saturated fatty acid is obtained.

Alternatively, wet cells or the culture broth can be subjected to direct extraction. In such a case, a water-miscible solvent such as methanol or ethanol, or a water-miscible solvent mixture comprising the water-miscible solvent and water or other organic solvent is used. The extraction procedure is the same as described for dried cells.

The lipid thus obtained contains highly unsaturated fatty acids in the form of a lipid compound such as fat. Although highly unsaturated fatty acids can be isolated in the form of free acids, they are preferably isolated in the form of an ester with a lower alcohol, for example, as methyl esters. By converting target fatty acids to such esters, each is easily separated from other lipid components, and from other target fatty acids and other undesirable fatty acids formed during culturing, such as palmitic acid, oleic acid, linoleic acid and the like, which are also esterified at the same time as the target fatty acids are esterified. To obtain methyl esters of the target fatty acids, for example, the lipid prepared as described above is treated with a 5 to 10% hydrochloric acid solution in absolute methanol or a 10 to 50% BF$_3$ solution in methanol for 1 to 24 hours at room temperature.

The mixture thus obtained is extracted with an organic solvent such as hexane, ethyl ether or ethyl acetate, to recover methyl esters of the target fatty acids. Next, the extract is dried over anhydrous sodium sulfate, and the solvent is distilled under reduced pressure to obtain a residue mainly comprising a fatty acid mixture. The mixture contains, in addition to methyl esters of the target highly unsaturated fatty acids, methyl palmitate, methyl stearate, methyl oleate and the like. From the mixture, methyl esters of highly unsaturated fatty acids are isolated by column chromatography, low temperature crystallization, an urea-adducting method, centrifugal partition chromatography, or a combination thereof.

The isolated methyl esters of the target fatty acids are then hydrolyzed with an alkali and extracted with an organic solvent such as ethyl ether, ethyl acetate, or the like to obtain the target fatty acids in a free form.

Alternatively, target fatty acids can be obtained, without conversion to methyl ester, by alkalolysis with, for example, 5% sodium hydroxide at a room temperature for 2 to 3 hours, followed by extraction of the fatty acids from the alkalolysis product and isolation of the target fatty acids.

In accordance with the present invention, both a mixture of highly unsaturated fatty acids and an individual fatty acid can be obtained. To produce an individual fatty acid, the above-mentioned mixture of methyl esters of highly unsaturated fatty acids or mixture of highly unsaturated fatty acids is subjected to a conventional separation procedure such as urea-adducting method, column chromatography, or the like.

EXAMPLES

The present invention will now be further illustrated by, but is by no means limited to, the following examples.

EXAMPLE 1

Production of highly unsaturated fatty acids 100 ml of a medium containing 2% glucose and 1% yeast extract (pH 6.0) was prepared and charged into a 500 ml-volume Meyer flask, and the whole was autoclaved for 20 minutes at 120° C. After cooling, Echinosporangium transversalis ATCC 16960; NRRL 3116 and ATCC 18036; NRRL 5525 were inoculated to the media, and then cultured for 8 days at 28° C. with reciprocal shaking at 110 rpm. After culturing, the cultured broth was filtered to recover cells; the cells were then completely washed with water and lyophilized to obtain 809 mg and 784 mg of dry cells respectively. The lyophilizates were extracted with a mono-phase solvent system consisting of chloroform/methanol/water according to a method of Bligh and Dyer to obtain 194.5 mg and 161.3 mg of lipids, respectively. The lipids were treated with absolute methanol/hydrochloric acid (10%) at 50° C. for 3 hours to methyl-esterify fatty acids contained in the lipids, to obtain 485 mg and 420 mg of fatty acid methyl esters, respectively. The composition of the methyl esters was analyzed by gas chromatography, and the results are shown in Table 1.

TABLE 1

| Ester | Strain | |
|---|---|---|
| | NRRL 3116 | NRRL 5525 |
| Methyl palmitate | 11.9 (%) | 12.2 (%) |
| Methyl stearate | 4.9 | 4.2 |
| Methyl oleate | 38.4 | 40.1 |
| Methyl linolate | 13.1 | 14.3 |
| Methyl γ-lenolenate | 5.5 | 5.1 |
| Methyl bishomo-γ-linolenate | 5.0 | 4.7 |
| Methyl arachidonate | 21.2 | 19.4 |

The fatty acid methyl ester mixture obtained from the strain ATCC 16960; NRRL 3116 was separated by column chromatography to obtain three fractions containing methyl γ-linolenate, methyl bishomo-γ-linolenate, and methyl arachidonate, respectively. By evaporating the solvent, methyl γ-linolenate 13.3 mg, methyl bishomo-γ-linolenate 12.1 mg, and methyl arachidonate 51.4 mg were obtained. The preparations prepared as above were compared with commercially available authentic preparations of methyl γ-linolenate, methyl bishomo-γ-linolenate and methyl arachidonate by gas chromatography, high performance liquid chromatography, mass spectrometry and NMR spectrometry, and as a result, it was found that the data of the preparations prepared as above conformed to those of the authentic samples.

EXAMPLE 2

First, 2 ml of a medium containing 2% glucose and 1% yeast extract supplemented with 0.5% hydrocarbon, fatty acid sodium salt or oil shown in Table 2 was put into 10 ml Erlenmeyer flasks and autoclaved at 120° C. for 20 minutes. Echinosporangium transversalis ATCC 16960; NRRL 3116 was inoculated to each medium, and cultured on a reciprocal shaker at 110 rpm, at 28° C. for 7 days. After culturing, each culture broth was filtered to recover cells, which were then thoroughly washed with water and dried by a centrifugal evaporator at 60° C. for 2 hours. The dried cells were than treated with 2 ml of methylene chloride and 2 ml of absolute methanol/hydrochloric acid (10%) at 50° C. for 3 hours, to methyl-esterify fatty acids, and to the mixture were added 4 ml of n-hexane and 1 ml of water to extract the methyl esters of fatty acids. The extraction was twice repeated. The extract was evaporated by a centrifugal evaporator at 40° C. for 1 hour to obtain a mixture of fatty acid methyl esters, which was then analyzed by gas chromatography. The results are shown in Table 2.

TABLE 2

| Additives | γ-linolenic acid (mg/ml) | Bishomo-γ-linolenic acid (mg/ml) | Arachidonic acid (mg/ml) |
|---|---|---|---|
| Hexadecane | 0.10 | 0.09 | 0.35 |
| Octadecane | 0.09 | 0.10 | 0.37 |
| Sodium stearate | 0.11 | 0.10 | 0.36 |
| Sodium oleate | 0.10 | 0.11 | 0.39 |
| Sodium linolate | 0.14 | 0.12 | 0.42 |
| Olive oil | 0.12 | 0.11 | 0.43 |
| Cottonseed oil | 0.09 | 0.09 | 0.37 |
| Coconut oil | 0.10 | 0.09 | 0.38 |
| Non addition | 0.09 | 0.08 | 0.34 |

As seen from Table 2, where hydrocarbon, fatty acid sodium salt or oil was added to a basal medium, the yield of highly unsaturated fatty acids was increased by 1 to 20%.

EXAMPLE 3

First, 2 ml of a medium containing 4% glucose, 1% yeast extract and 2% sesame oil (pH 6.0); 2 ml of a medium containing 4% glucose, 1% yeast extract and 2% peanut oil (pH 6.0); 2 ml of a medium containing 4% glucose, 1% yeast extract and 2% olive oil (pH 6.0); and 2 ml a medium containing 4% glucose and 1% yeast extract (pH 6.0) was put into 10 ml Erlenmeyer flasks, and autoclaved at 120° C. for 20 minutes., Echinosporangium transversalis ATCC 16960; NRRL 3116 was inoculated to each medium, and cultured on a reciprocal shaker at 110 rpm, at 28° C. for 7 days. After culturing, filtration, washing with water, drying, hydrolysis, methyl-esterification and extraction, as well as an analysis of resulting fatty acid methyl esters, were carried out according to the procedure described in Example 2. The results are shown in Table 3.

TABLE 3

| Additives | Dried cells (g/l) | Bishomo-γ-linolenic acid (mg/l) | Arachidonic acid (mg/l) |
|---|---|---|---|
| Non addition | 12.89 | 205.0 | 538.8 |
| Peanut oil | 15.02 | 319.9 | 473.1 |
| Sesame oil | 14.47 | 438.4 | 153.4 |
| Olive oil | 15.23 | 223.8 | 554.3 |

As seen from Table 3, the addition of sesame oil or peanut oil decreases the production of arachidonic acid and increases the production of bishomo-γ-linolenic acid. On the other hand, the addition of olive oil did not increase the production of bishomo-γ-linolenic acid.

From the above results, it is obvious that an extract obtained by an extraction of sesame oil with an organic solvent, and effective ingredients contained in the extract, i.e., sesamin (2,6-bis-(3,4-methylenedioxyphenyl)-cis-3,7-dioxabicyclo [3.3.0] octane), sesaminol (2-(3,4-methylenedioxy-6-hydroxyphenyl)-6-(3,4-methylenedioxyphenyl)-cis-3,7-dioxabicyclo [3.3.0] octane), episesamin and episesaminol, as well as sesamolin derived from crude sesame oil, and effective ingredients contained in acetone extract from sesame seeds, i.e., 2-(3,4-methylenedioxyphenyl)-6-(3-methoxy-4-hydroxyphenyl)-3,7-dioxabicyclo [3.3.0] octane, 2,6-bis-(3-methoxy-4-hydroxyphenyl)-3,7-dioxabicyclo [3.3.0] octane, 2-(3,4-methylenedioxyphenyl)-6-(3-methoxy-4-hydroxyphenoxy)-3,7-dioxabicyclo [3.3.0] octane effectively increase the yield of bishomo-γ-linolenic acid (see Japanese Patent Application No. 63-53642).

EXAMPLE 4

First, 2 ml of a medium containing 4% glucose, 1% yeast extract, and 0.01% sesamin or episesamin (pH 6.0) was put into 10 ml Erlenmeyer flasks, and autoclaved at 120° C. for 20 minutes. *Echinosporangum transversalis* ATCC 16960; NRRL 3116 was inoculated into the medium and cultured on a reciprocal shaker at 110 rpm, at 28° C. for 7 days. After culturing, filtration, washing with water, drying, hydrolysis, methyl esterification, and extraction were carried out according to the procedure described in Example 2, and the obtained fatty acid methyl esters were analyzed by gas chromatography. The addition of sesamin or episesamin increased the production of bishomo-γ-linolenic acid, and where sesamin was added, an amount of bishomo-γ-linolenic acid was 401.3 mg/l both, and where episesamin was added, it was 383.5 mg/l.

EXAMPLE 5

First, 4 ml of a medium containing 4% glucose and 1% yeast extract (pH 6.0) was put into 20 ml Erlenmeyer flasks, and autoclaved at 120° C. for 20 minutes. *Echinosporangium transversalis* ATCC 16960; NRRL 3116 was inoculated to the media, and cultured on a reciprocal shaker at 110 rpm, at 28° C. for 2 days. After the culturing, 80 mg (2%) sesame oil or 0.4 mg (0.01%) sesamin was added to the culture, followed by further culturing for 6 days. Filtration, washing with water, drying, hydrolysis, methyl-esterification and extraction were carried out according to the procedure described in Example 2, and resulting fatty acid methyl esters were analyzed by gas chromatography. The addition of sesame oil or sesamin during the culturing increased the yield of bishomo-γ-linolenic acid per broth. The addition of sesame oil provided 440.3 mg/l bishomo-γ-linolenic acid, and the addition of sesamin provided 412.7 mg/l.

EXAMPLE 6

0.5 g each of spices, i.e., Tarragon, Dill Seed, Parsley, Turmeric, and Nutmeg, were separately added to 5 ml of dichloromethane, each mixture was ground in a mortar with a pestle to extract ingredients, and the whole was centrifuged to obtain a supernatant, which was then evaporated to obtain an extract. Each extract obtained from the above-mentioned spices was dissolved in 4 ml of ethanol to prepare a solution.

On the other hand, aqueous solutions of 4 mg/ml of uracil, cytocine, adenine, guanine and hypoxanthine were prepared.

10 ml each of a medium containing 4% glucose and 1% yeast extract (pH 6.0) was put into test tubes, and autoclaved, and to the test tubes were added 50 μl of the above-prepared solutions, and *Echinosporangium transversalis* ATCC 16961; NRRL 3116 was inoculated to the media. Culturing was carried out for six days at 28° C. with shaking at 300 rpm, cells were obtained from each cultured broth, and the cells were treated by the same procedures as described in Example 2, to determine the amount of bishomo-γ-linolenic acid obtained from each culture. The results are shown in Table 4.

TABLE 4

| Additive | Amount of bishomo-γ-linolenic acid produced (g/l broth) |
|---|---|
| | Amount of product |
| Tarragon extract | 0.32 |
| Dill Seed extract | 0.28 |
| Parsley extract | 0.26 |
| Turmeric extract | 0.40 |
| Nutmeg extract | 0.30 |
| Uracil | 0.22 |
| Cytocine | 0.20 |
| Adenine | 0.25 |
| Guanine | 0.23 |
| Hypoxanthine | 0.21 |

As a comparison, an amount of bishomo-γ-linolenic acid produced from a culture without an additive was 0.14 g/l.

We claim:

1. A process for production of a highly unsaturated fatty acid, comprising the steps of:
   culturing a microorganism capable of synthesizing a highly unsaturated fatty acid containing at least three double bonds in the carbon chain and having 20 or 22 carbon atoms, said microorganism belonging to the genus Echinosporangium; and
   recovering the highly unsaturated fatty acid so produced, said acid having at least three double bonds in the carbon chain and having 20 or 22 carbon atoms.

2. A process according to claim 1, wherein the microorganism is *Echinosporangium transversalis*.

3. A process according to claim 2, wherein the *Echinosporangium transversalis* is *Echinosporangium transversalis* ATCC 16960 or ATCC 18036.

4. A process according to claim 1, wherein the fatty acid is bishomo-γ-linolenic acid, arachidonic acid, eicosapentaenoic acid, or docosahexaenoic acid.

5. A process according to claim 4, wherein to produce bishomo-γ-linolenic acid, an additive selected from the group consisting of sesame oil, peanut oil, sesamin, sesaminol, episesamin, episesaminol, sesamolin, 2-(3,4-methylenedioxyphenyl)-6-(3-methoxy-4-hydroxyphenyl)-3,7-dioxabicyclo [3.3.0] octane, 2,6-bis(3-methoxy-4-hydroxy-phenyl)-3,7-dioxabicyclo [3.3.0] octane and 2-(3,4-methylenedioxyphenyl)-6-(3-methoxy-4-hydroxyphenoxy) -3,7-dioxabicyclo [3.3.0] octane is added to a medium at the start of culturing or during culturing.

6. A process for the production of a lipid containing a highly unsaturated fatty acid, comprising the steps of:
culturing a microorganism capable of synthesizing a highly unsaturated fatty acid containing at least three double bonds in the carbon chain and having 20 or 22 carbon atoms, said microorganism belonging to the genus Echinosporangium; and
recovering the lipid containing highly unsaturated fatty acid, said acid having at least three double bonds in the carbon chain and having 20 or 22 carbon atoms.

7. A process according to claim 6, wherein the lipid-containing fatty acid is lipid-containing bishomo-γ-linolenic acid, arachidonic acid, eicosapentaenoic acid or docosahexaenoic acid.

8. A process according to claim 6, wherein an additive selected from the group consisting of sesame oil, peanut oil, sesamin, sesaminol, episesamin, episesaminol, sesamolin, 2-(3,4-methylenedioxyphenyl)-6-(3-methoxy-4-hydroxyphenyl)-3,7-dioxabicyclo [3.3.0] octane, 2,6-bis-(3-methoxy-4-hydroxyphenyl)-3,7-dioxabicyclo [3.3.0] octane and 2-(3,4-methylenedioxyphenyl)-6-(3-methoxy-4-hydroxyphenoxy) -3,7-dioxabicyclo [3.3.0] octane is added to a medium at the start of culturing or during culturing.

9. A process according to claim 6, wherein the microorganism is *Echinosporangium transversalis*.

10. A process according to claim 9, wherein the *Echinosporangium transversalis* is *Echinosporangium transversalis* ATCC 16960 or ATCC 18036.

* * * * *